(12) United States Patent
Hayes

(10) Patent No.: US 12,169,231 B2
(45) Date of Patent: Dec. 17, 2024

(54) SYSTEM AND METHOD FOR MEDICAL SIMULATION

(71) Applicant: Global Diagnostic Imaging Solutions, LLP, Orlando, FL (US)

(72) Inventor: Matthew Hayes, Cary, NC (US)

(73) Assignee: MediSim Technologies, Inc., Orlando, FL (US)

( * ) Notice: Subject to any disclaimer, the term of this patent is extended or adjusted under 35 U.S.C. 154(b) by 226 days.

(21) Appl. No.: 17/533,967

(22) Filed: Nov. 23, 2021

(65) Prior Publication Data
US 2022/0252687 A1     Aug. 11, 2022

Related U.S. Application Data

(60) Provisional application No. 63/117,869, filed on Nov. 24, 2020.

(51) Int. Cl.
*G01R 33/56*     (2006.01)
*A61B 5/00*      (2006.01)
(Continued)

(52) U.S. Cl.
CPC .......... *G01R 33/5608* (2013.01); *A61B 5/055* (2013.01); *A61B 5/743* (2013.01);
(Continued)

(58) Field of Classification Search
CPC .............. G01R 33/5608; G01R 33/546; G01R 33/288; G01R 33/54; A61B 5/055;
(Continued)

(56) References Cited

U.S. PATENT DOCUMENTS 8,920,176 B1 * 12/2014 Yang ................. G09B 23/30
434/262
2005/0277096 A1    12/2005 Hendrickson et al.
(Continued)

FOREIGN PATENT DOCUMENTS

CN     108888340 A  * 11/2018
JP     2017140165 A    8/2017

OTHER PUBLICATIONS

Comparison of apparent diffusion coefficient values among different MRI platforms: a multicenter phantom study Kvrak et. al., Sep. 2013 (Year: 2013).*
(Continued)

*Primary Examiner* — Keith M Raymond
*Assistant Examiner* — Fikirte (Fiki) T Ashine
(74) *Attorney, Agent, or Firm* — Locke Lord LLP; Christopher J. Capelli

(57) ABSTRACT

Computer simulation of a Magnetic Resonance Imaging (MRI) medical imaging examination procedures by visually displaying, for user selection, MRI settings associated with third party MRI vendors. Critical questions are displayed relating to a user selected simulated MRI examination procedure. A user selected MRI examination procedure is simulated by generating resulting MRI images, which are displayed to the user. A deviation value is generated correlating to deviation of the generated resulting MRI images from acceptable MRI images relating to the user selected MRI examination procedure. A score value is determined for the user's simulated MRI examination procedure based upon the determined deviation value and the user's response to the one or more critical questions.

20 Claims, 23 Drawing Sheets

(51) Int. Cl.
  *A61B 5/055*   (2006.01)
  *G01R 33/54*   (2006.01)
  *G16H 50/50*   (2018.01)
(52) U.S. Cl.
  CPC .......... *A61B 5/7435* (2013.01); *G01R 33/546* (2013.01); *G16H 50/50* (2018.01)
(58) Field of Classification Search
  CPC ..... A61B 5/743; A61B 5/7435; A61B 5/0013; G16H 50/50; G16H 30/20; G09B 23/286
  See application file for complete search history.

(56) References Cited

U.S. PATENT DOCUMENTS

| | | | |
|---|---|---|---|
| 2015/0254422 A1 | 9/2015 | Avisar | |
| 2016/0314710 A1* | 10/2016 | Jarc | G09B 23/28 |
| 2018/0098813 A1* | 4/2018 | Nesichi | G09B 23/28 |
| 2018/0231628 A1* | 8/2018 | Kuang | G01R 33/56536 |
| 2019/0214149 A1 | 7/2019 | Volkar et al. | |
| 2020/0105070 A1* | 4/2020 | Coustaud | G06T 19/20 |
| 2021/0307831 A1* | 10/2021 | Fuerst | G09B 23/30 |

OTHER PUBLICATIONS

International Search Report and Written Opinion for PCT Application No. PCT/US2021/060522, dated Mar. 14, 2022.
International Preliminary Report on Patentability for PCT Application No. PCT/US2021/060522, dated Jun. 8, 2023.

* cited by examiner

566

Critical Thinking Question

- O
- O
- O
- O
- O

Critical Thinking Question

Select the parameters that would result in T1 weighted images

- O  TR 500ms, TE 100ms
- O  TR 5000ms, TE 15ms
- O  TR 500ms, TE 15ms
- O  TR 5000ms, TE 100ms

Critical Thinking Question

- O All of following can lead to a reduction in patient motion artifacts in MRI images except.
- O
- O
- O
- O

FIG. 5N

Angio Timing Examinations 568
Based on a time to center (TTC) of 2.1 seconds, please select the appropriate arrival time of contrast.
Based on a time to center (TTC) of 2.1 seconds, please select the appropriate arrival time to contrast
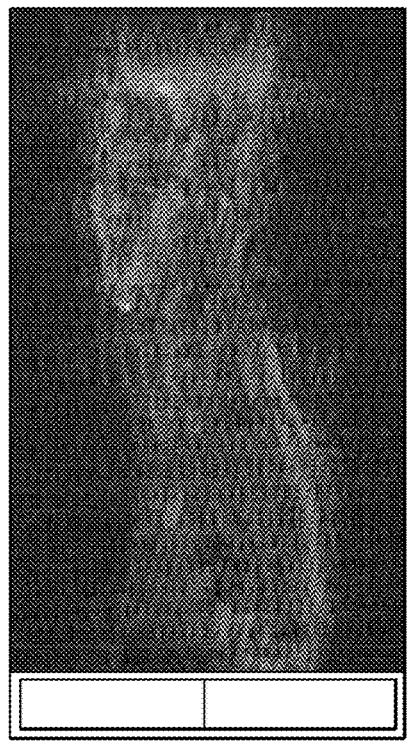
FIG. 50

572

Test Results                    98.4%

MRI

| | ✓ v |
| | ✓ v |
| | ✓ v |
| | ✓ v |
| | ✓ ∧ |

RETURN TO TEST SELECTION

New Cohort

Name _____

[Create]

2 Student(s)

Student Manager

☐ Critical Thinking Averages

Find Student 🔍

_____

_____

Rows per page: 1-2 of 2 ‹ ›

FIG. 5R

SYSTEM AND METHOD FOR MEDICAL SIMULATION

CROSS REFERENCE TO RELATED APPLICATIONS

This application claims priority to U.S. Patent Application Ser. No. 63/117,869 filed Nov. 24, 2020 which is incorporated herein by reference in its entirety.

FIELD OF THE INVENTION

The disclosed embodiments generally relates to a system, software, and method for simulating interactions between a medical device and one or more body tissues during a medical procedure and more particularly, to simulation of a Magnetic Resonance Imaging (MRI) medical procedure.

BACKGROUND OF THE INVENTION

The life sciences industry has long struggled to find applications for simulation software due to the complex nature of soft tissue and human biology as compared to the more predictable properties of fluid dynamics, mechanical engineering, and electromagnetic engineering. Yet recent advances in the field have opened the doors to new uses for CAE simulation that are transforming the industry.

With increasingly accurate methodologies capable of modeling tissues, organs, and the human musculoskeletal structure, medical device companies are now able to demonstrate the effectiveness and safety of their devices with greater confidence, prior to launching a clinical trial. Simulation also helps researchers test novel treatments without risking patient health, leading to a faster development of new devices, biotech, and pharmaceuticals.

Image-guided medical procedures, such as minimally invasive percutaneous medical procedures, require use of medical images in conjunction with delicate and complex skill process for taking proper images, such as during an MRI procedure. Without performing the procedures often in patients, it is difficult for a health care worker, such as a MRI technician, to maintain the high degree of skill needed to perform these procedures or to implement new methods, operations and procedures. In addition, there is currently no way for MRI technicians to realistically evaluate different approaches to treatment options for patient specific situations prior to actually performing the procedures in the patient.

Systems for simulating medical procedures have provided important training tools that allow technicians to develop skills that can be transferred to actual imaging of a patient. With specific regard to MRI imaging, it is to be understood and appreciated that MRI slice prescription on patients is highly subjective and non-uniform across practitioners throughout the world.

Accordingly, there is a need to provide a computer simulation system that quantifies practical clinical skills based on a deviation from a master angle, slice positioning, slice coverage and scan parameters regarding MRI techniques.

SUMMARY OF THE INVENTION

The purpose and advantages of the below described illustrated embodiments will be set forth in and apparent from the description that follows. Additional advantages of the illustrated embodiments will be realized and attained by the devices, systems and methods particularly pointed out in the written description and claims hereof, as well as from the appended drawings.

MRI slice prescription on patients has always been very subjective and non-uniform across practitioners throughout the world. Provided is a simulation system to quantify practical clinical skills based on a deviation from a master angle, slice positioning, slice coverage and scan parameters. For instance, when a technician is using the simulator, the technician positions the slices and adjusts parameters. It is to be appreciated that there is an acceptable range of slices, slice angulation, field of view, and overall slice coverage that does not result in a loss of points regarding a score generated by the simulator. However, after a certain amount of deviation to any of the acceptable ranges, points are deducted from the user's generated score.

Preferably, the MRI simulator is a web application available for use with any computer having an internet connection. In use, a practitioner/technician preferably selects a preferred scanner and chooses an anatomic model (a patient), then uses the same interface as on real scanners to set the MRI slice positions, pulse sequence and its parameters. After running the simulated scan utilizing stored MRI images, the MRI simulator returns the same resulting images as on a real scanner with a live patient, including noise and artifacts.

To achieve these and other advantages and in accordance with the purpose of the illustrated embodiments, in one aspect described is web based simulator application configured to provide student MRI user's to be graded based on expertise and vocation mastery. For instance, grading may be provided on the following exemplary acceptable MRI ranges: correct slice angles; how large or small the field of imaging is; how thick a slice can be; how many slices are needed to cover a certain body part (e.g. a brain, wrist, knee); how much space is between slices; image parameters that make an image look a certain way (fluid dark, fat bright, etc). And based on the user's deviation from the correct ranges, a score is generated whereby points may be deducted for improper deviation while providing internal gradient rubric and algorithm. For instance, after completion of a simulated MRI exam, the user is preferably presented with a variety of multiple choice questions covering varying topics (e.g., anatomy and pathology) with the goal of simulating thought processes that would occur during a typical in person clinical examination. The multiple choice questions may be sorted into various categories and presented so as to reproduce the skill/thought processes required for performing an MRI examination on an actual patient.

In accordance with an illustrated embodiment, described herein is a computer system and method for providing simulation of a Magnetic Resonance Imaging (MRI) medical imaging procedure, in which visually displayed on a user's computer terminal (e.g., GUI), for user selection, is one or more criteria for initiating simulation of a MRI procedure. Additionally, visually displayed on the user's terminal, for user selection, are one or more MRI examination procedures to be simulated based upon the user selected criteria for simulation of a MRI procedure. And also preferably visually displayed on the user terminal is a virtual MRI interface for accepting user input for configuring imaging to be initiated for a user selected MRI examination procedure to be simulated based upon the user selected criteria for simulation of a MRI procedure. One or more critical questions are also preferably displayed on a GUI presented to the user relating to the user selected MRI examination procedure to be simulated based upon the user selected criteria for simulation of a MRI procedure, wherein a user provides one or more responses to the one or more critical questions. A computer processor than simulates the user selected MRI examination procedure based upon the user selected criteria for simulation of the MRI procedure to generate resulting MRI images, preferably displayed to the user, via a GUI. The computer processor, preferably based upon prescribed criteria, determines a deviation value from which the generated resulting MRI images deviate from acceptable MRI images relating to the user selected MRI examination procedure, with the computer processor also determining a score value for the user's simulated MRI examination procedure based upon the determined deviation value and the user's response to the one or more critical questions.

BRIEF DESCRIPTION OF THE DRAWINGS

The accompanying appendices and/or drawings illustrate various non-limiting, example, inventive aspects in accordance with the present disclosure.

DETAILED DESCRIPTION OF CERTAIN EMBODIMENTS

Figure 1:
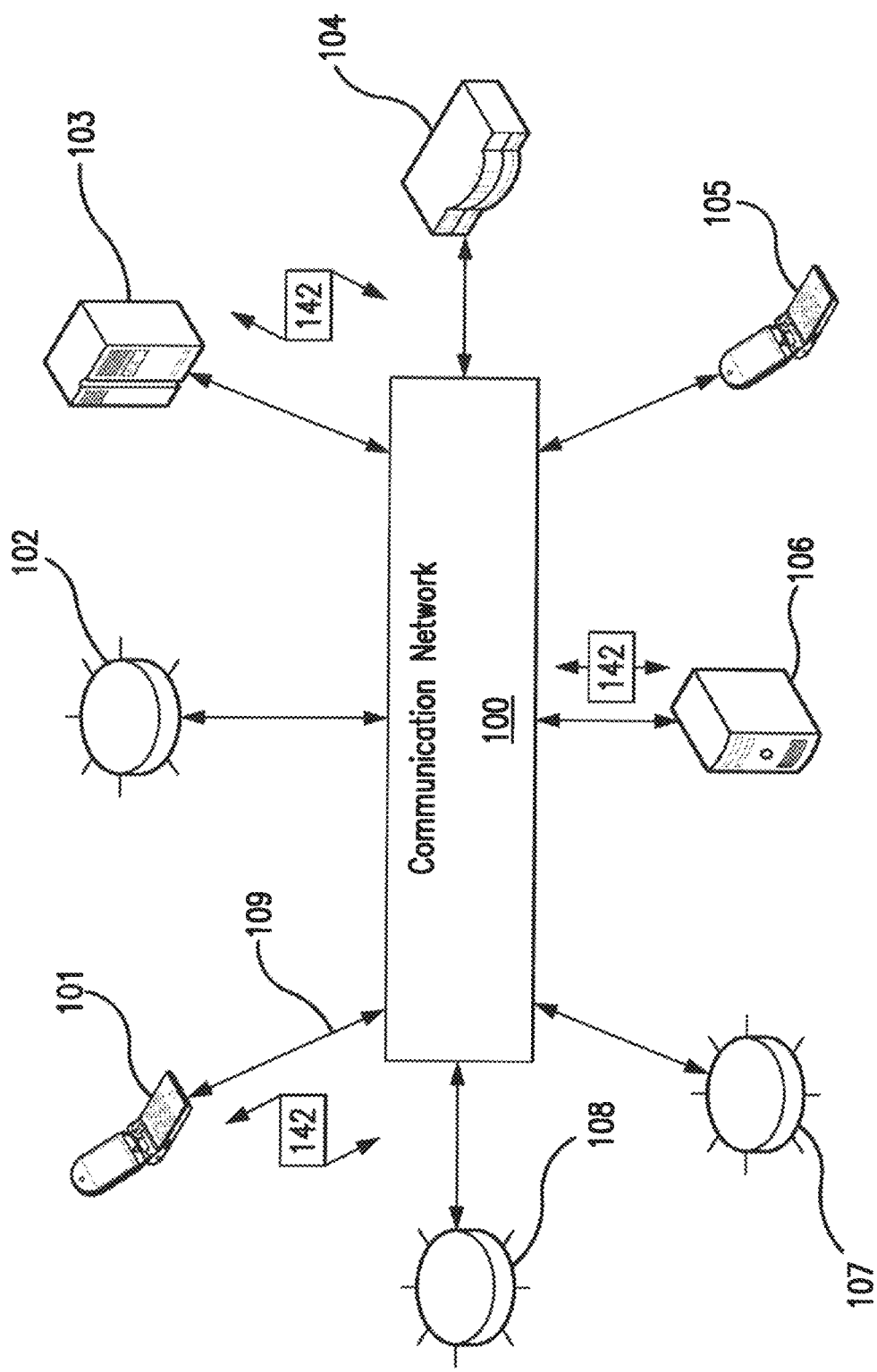
FIG. 1 illustrates an exemplary system overview and data-flow for use with an illustrated embodiment for depicting system operation.

The illustrated embodiments are now described more fully with reference to the accompanying drawings wherein like reference numerals identify similar structural/functional features. The illustrated embodiments are not limited in any way to what is illustrated as the illustrated embodiments described below are merely exemplary, which can be embodied in various forms, as appreciated by one skilled in the art. Therefore, it is to be understood that any structural and functional details disclosed herein are not to be interpreted as limiting, but merely as a basis for the claims and as a representation for teaching one skilled in the art to variously employ the discussed embodiments. Furthermore, the terms and phrases used herein are not intended to be limiting but rather to provide an understandable description of the illustrated embodiments.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the illustrated embodiments, exemplary methods and materials are now described.

It must be noted that as used herein and in the appended claims, the singular forms "a", "an," and "the" include plural referents unless the context clearly dictates otherwise. Thus, for example, reference to "a stimulus" includes a plurality of such stimuli and reference to "the signal" includes reference to one or more signals and equivalents thereof known to those skilled in the art, and so forth.

It is to be appreciated the illustrated embodiments discussed below are preferably a software algorithm, program or code residing on computer useable medium having control logic for enabling execution on a machine having a computer processor for simulating interactions between a medical device and one or more tissues during a medical procedure. The machine typically includes memory storage configured to provide output from execution of the computer algorithm or program.

As used herein, the term "software" is meant to be synonymous with any code or program that can be in a processor of a host computer, regardless of whether the implementation is in hardware, firmware or as a software computer product available on a disc, a memory storage device, or for download from a remote machine. The embodiments described herein include such software to implement the equations, relationships and algorithms described above. One skilled in the art will appreciate further features and advantages of the illustrated embodiment's based on the above-described embodiments. Accordingly, the illustrated embodiments are not to be limited by what has been particularly shown and described, except as indicated by the appended claims.

Turning now descriptively to the drawings, in which similar reference characters denote similar elements throughout the several views, FIG. 1 depicts an exemplary computer communications network 100 in which below illustrated embodiments may be implemented.

It is to be understood a communication network 100 is a geographically distributed collection of nodes interconnected by communication links and segments for transporting data between end nodes, such as personal computers, work stations, smart phone devices, tablets, televisions, sensors and or other devices such as automobiles, etc. Many types of networks are available, with the types ranging from local area networks (LANs) to wide area networks (WANs). LANs typically connect the nodes over dedicated private communications links located in the same general physical location, such as a building or campus. WANs, on the other hand, typically connect geographically dispersed nodes over long-distance communications links, such as common carrier telephone lines, optical lightpaths, synchronous optical networks (SONET), synchronous digital hierarchy (SDH) links, or Powerline Communications (PLC), and others.

FIG. 1 is a schematic block diagram of an example communication network 100 illustratively comprising nodes/user devices 101-108 (e.g., sensors 102, client computing devices 103, smart phone devices 105, web servers 106, routers 107, switches 108, and the like) interconnected by various methods of communication. For instance, the links 109 may be wired links or may comprise a wireless communication medium, where certain nodes are in communication with other nodes, e.g., based on distance, signal strength, current operational status, location, etc. Moreover, each of the devices can communicate data packets (or frames) 142 with other devices using predefined network communication protocols as will be appreciated by those skilled in the art, such as various wired protocols and wireless protocols etc., where appropriate. In this context, a protocol consists of a set of rules defining how the nodes interact with each other. Those skilled in the art will understand that any number of nodes, devices, links, etc. may be used in the computer network, and that the view shown herein is for simplicity. Also, while the embodiments are shown herein with reference to a general network cloud, the description herein is not so limited, and may be applied to networks that are hardwired.

As will be appreciated by one skilled in the art, aspects of the illustrated embodiments may be embodied as a system, method or computer program product. Accordingly, aspects of the illustrated embodiments may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, aspects of the illustrated embodiment's may take the form of a computer program product embodied in one or more computer readable medium(s) having computer readable program code embodied thereon.

Any combination of one or more computer readable medium(s) may be utilized. The computer readable medium may be a computer readable signal medium. A computer readable storage medium may be, for example, but not limited to, an electronic, magnetic, optical, electromagnetic, infrared, or semiconductor system, apparatus, or device, cloud service or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, an or any suitable combination of the foregoing. In the context of this document, a computer readable storage medium may be any tangible medium that can contain, or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electromagnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium may be transmitted using any appropriate medium, including but not limited to wireless, wireline, optical fiber cable, RF, etc., or any suitable combination of the foregoing.

Computer program code for carrying out operations for aspects of the illustrated embodiments may be written in any combination of one or more programming languages, including an object oriented programming language such as Java, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Aspects of the illustrated embodiments are described below with reference to flowchart illustrations and/or block diagrams of methods, apparatus (systems) and computer program products according to embodiments of the illustrated embodiments. It will be understood that each block of the flowchart illustrations and/or block diagrams, and combinations of blocks in the flowchart illustrations and/or block diagrams, can be implemented by computer program instructions. These computer program instructions may be provided to a processor of a special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

Figure 2:
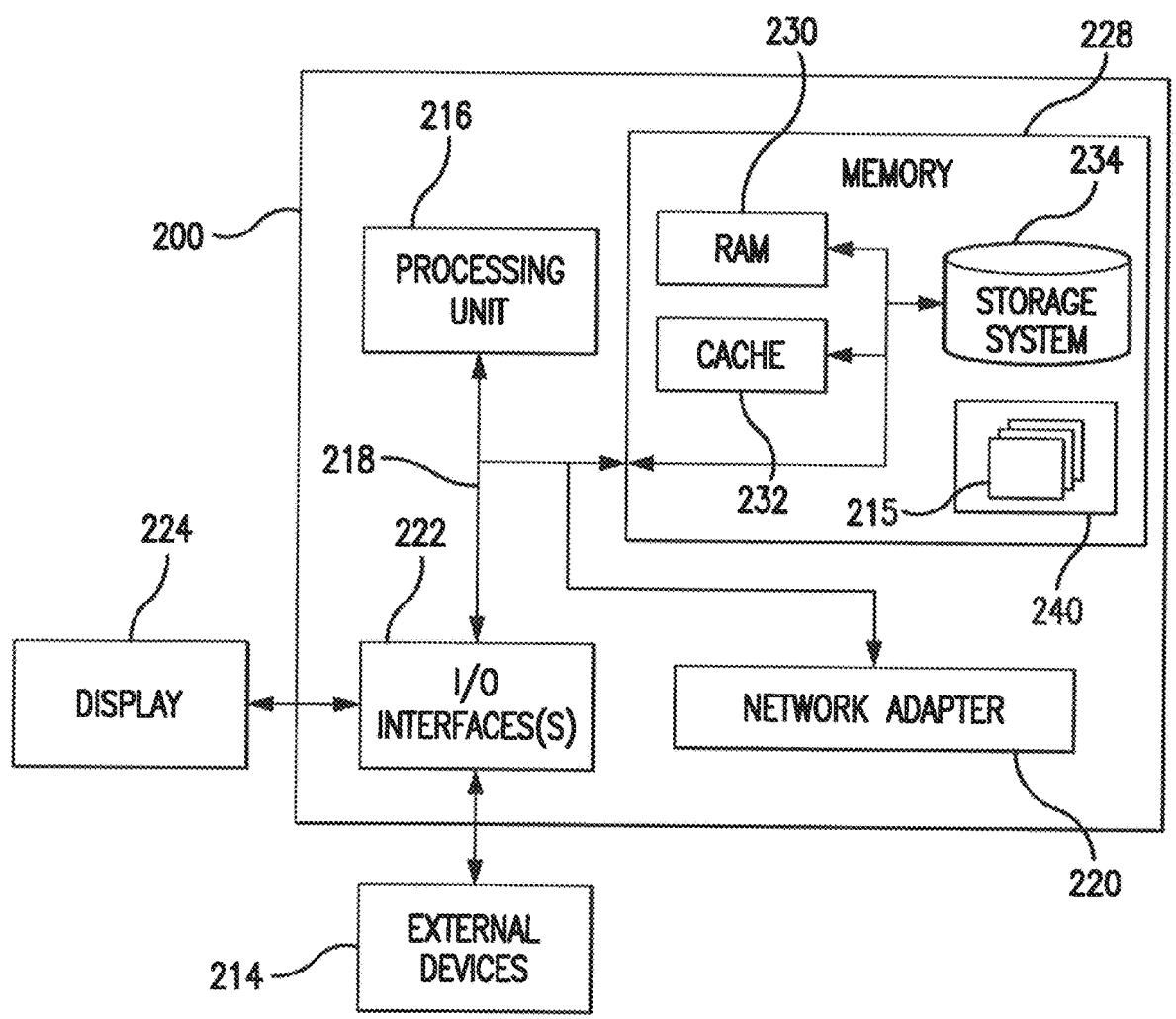
FIG. 2 illustrates an example computing device configured in accordance with the illustrated embodiments.

With reference now to FIG. 2, shown is a schematic block diagram of an example network user computing device 200 (e.g., client computing devices 103 and/or web servers 106, etc.) that may be used (or components thereof) with one or more illustrated embodiments described herein. As explained above, in different embodiments these various devices are configured to communicate with each other in any suitable way, such as, for example, via communication network 100.

Device 200 is intended to represent any type of user computer system capable of carrying out the teachings of various embodiments of the illustrated embodiments. Device 200 is only one example of a suitable system and is not intended to suggest any limitation as to the scope of use or functionality of embodiments of the illustrated embodiments described herein. Regardless, device 200 is capable of being implemented and/or performing any of the functionality set forth herein.

Computing device 200 is operational with numerous other general purpose or special purpose computing system environments or configurations, such as client computing devices 103 and/or web servers 106. Computing device 200 may be described in the general context of computer system-executable instructions, such as program modules, being executed by a computer system. Generally, program modules may include routines, programs, objects, components, logic, data structures, and so on that perform particular tasks or implement particular abstract data types. Device 200 may be practiced in distributed data processing environments where tasks are performed by remote processing devices that are linked through a communications network. In a distributed data processing environment, program modules may be located in both local and remote computer system storage media including memory storage devices.

Device 200 is shown in FIG. 2 in the form of a computing device, such as client computing devices 103 and/or web servers 106, etc. The components of device 200 may include, but are not limited to, one or more processors or processing units 216, a system memory 228, and a bus 218 that couples various system components including system memory 228 to processor 216 and one or more camera components.

Bus 218 represents one or more of any of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnect (PCI) bus.

Device 200 typically includes a variety of computer system readable media. Such media may be any available media that is accessible by device 200, and it includes both volatile and non-volatile media, removable and non-removable media.

System memory 228 can include computer system readable media in the form of volatile memory, such as random access memory (RAM) 230 and/or cache memory 232. Computing device 200 may further include other removable/non-removable, volatile/non-volatile computer system storage media. By way of example only, storage system 234 can be provided for reading from and writing to a non-removable, non-volatile magnetic media (not shown and typically called a "hard drive"). As will be further depicted and described below, memory 228 may include at least one program product having a set (e.g., at least one) of program modules that are configured to carry out the functions of embodiments of the invention.

Program/utility 240, having a set (at least one) of program modules 215, such as underwriting module, may be stored in memory 228 by way of example, and not limitation, as well as an operating system, one or more application programs, other program modules, and program data. Each of the operating system, one or more application programs, other program modules, and program data or some combination thereof, may include an implementation of a networking environment. Program modules 215 generally carry out the functions and/or methodologies of embodiments of the illustrated embodiments as described herein.

Device 200 may also communicate with one or more external devices 214 such as a keyboard, a pointing device, one or more camera components, a display 224, etc.; one or more devices that enable a user to interact with computing device 200; and/or any devices (e.g., network card, modem, etc.) that enable computing device 200 to communicate with one or more other computing devices. Such communication can occur via Input/Output (I/O) interfaces 222. Still yet, device 200 can communicate with one or more networks such as cellular networks (e.g., TDMA, CDMA, 4g and 5g); a local area network (LAN), a general wide area network (WAN), and/or a public network (e.g., the Internet) via network adapter 220. As depicted, network adapter 220 communicates with the other components of computing device 200 via bus 218. It should be understood that although not shown, other hardware and/or software components could be used in conjunction with device 200. Examples, include, but are not limited to: microcode, device drivers, redundant processing units, external disk drive arrays, RAID systems, tape drives, and data archival storage systems, etc.

FIGS. 1 and 2 are intended to provide a brief, general description of an illustrative and/or suitable exemplary environment in which embodiments of the below described illustrated embodiments may be implemented. FIGS. 1 and 2 are exemplary of a suitable environment and are not intended to suggest any limitation as to the structure, scope of use, or functionality of an embodiment of the illustrated embodiments. A particular environment should not be interpreted as having any dependency or requirement relating to any one or combination of components illustrated in an exemplary operating environment. For example, in certain instances, one or more elements of an environment may be deemed not necessary and omitted. In other instances, one or more other elements may be deemed necessary and added.

Figure 3:
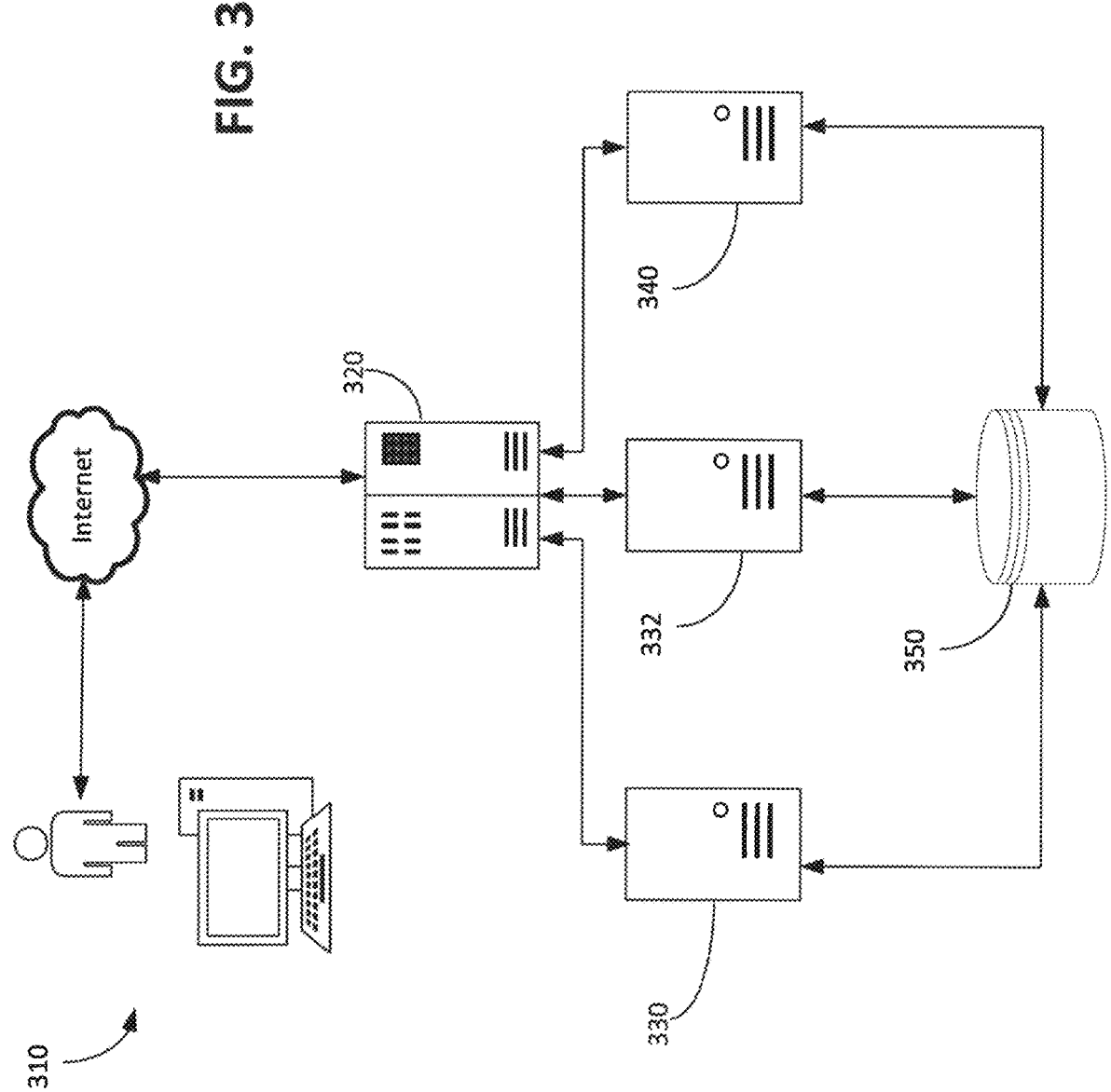
FIG. 3 illustrates an exemplary computer system in accordance with exemplary illustrated embodiments which incorporates aspects of the system of FIG. 1 and device of FIG. 2.

With reference now to FIG. 3, depicted is an exemplary computing system 300 for one or more below described illustrated embodiments for providing a computerized simulator specifically configured to provide training for, and evaluation of, medical practitioners regarding Magnetic Resonance Imaging (MRI) medical procedures. As shown, computing system preferably includes a web application server 320 that a user 310 (e.g., student and/or student manger) interacts with, preferably via a network 100 (e.g., the Internet). As shown in the illustrated embodiment of FIG. 3, coupled to the web application server 320 is a Contrast Lab Application Program Interface 330 and Resolution Lab Application Program Interface 332 preferably providing a complex dataset of MRI imaging maps, as discussed further below. Also coupled to the web application server 320 is preferably a ScanLabMR API 340, which is coupled to a ScanLabMR Database 350, preferably providing a repository of MRI images used to the facilitate the below described MRI simulation training and evaluation process 400.

With the exemplary communication network 100 (FIG. 1), computing device 200 (FIG. 2), and computer network system environment 300 (FIG. 3) being generally shown and discussed above, description of certain illustrated embodiments of the present invention will now be provided.

Figure 4:
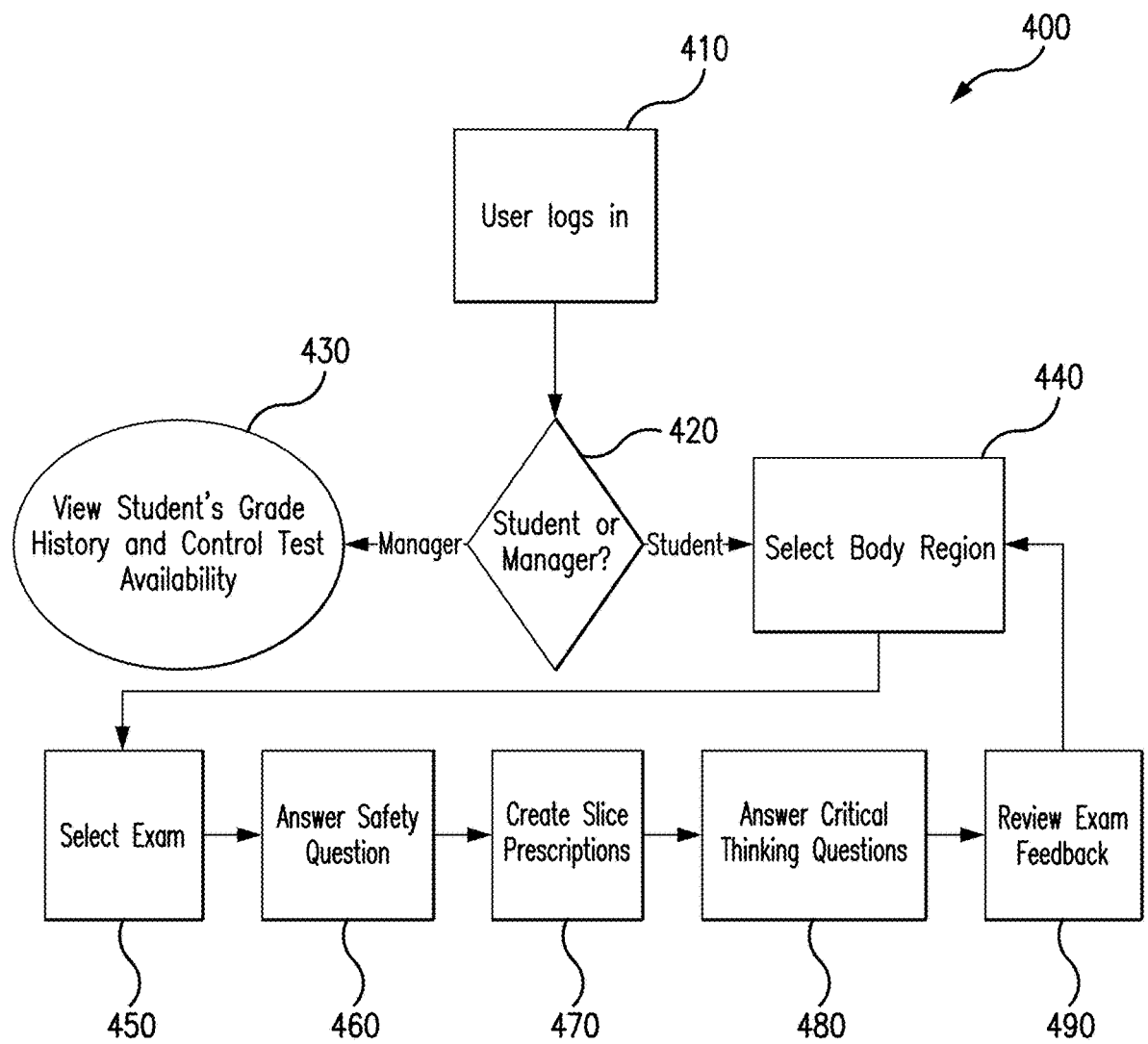
FIG. 4 illustrates a flow chart depicting operation of an MRI simulation process in accordance with exemplary illustrated embodiments and in conjunction with the system of FIG. 3.
Figure 5A:
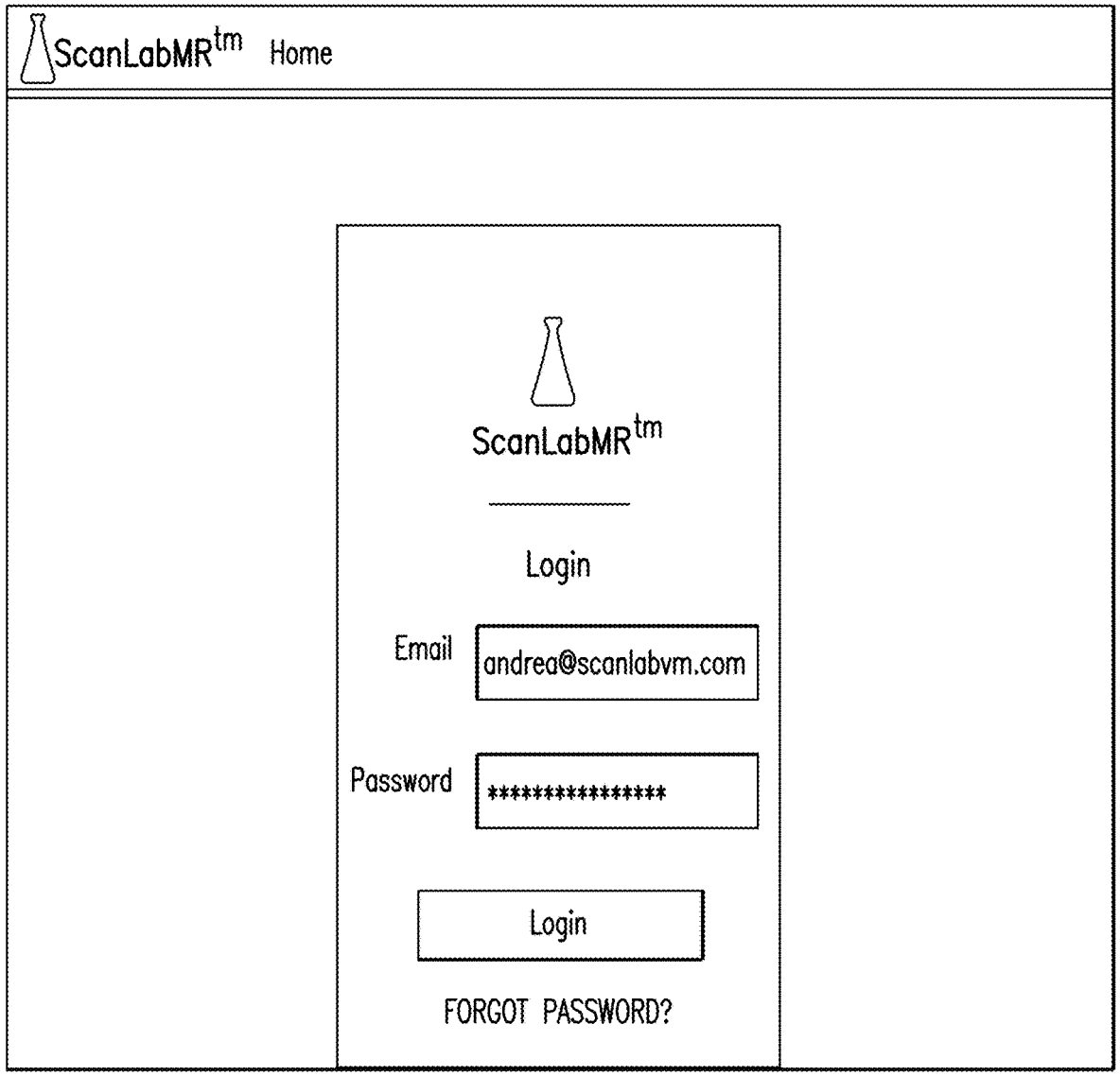
FIGS. 5A-5S illustrate various screen shots regarding operation of an MRI simulation process in accordance with exemplary illustrated embodiments.

With reference now to process 400 depicted in FIG. 4, and in conjunction with reference to certain screen shots depicted in FIGS. 5A-5Q, described is a computer apparatus, system and method configured to quantify practical clinical skills upon a practitioner based on a deviation from a master angle, slice positioning, slice coverage and numerous other scan parameters regarding MRI Imaging. Additionally, process 400 in accordance with the illustrated embodiments provides for a mentor/manager of the practitioner/user to evaluate the MRI imaging skills of the practitioner/user preferably based on a scoring system, as well as to provide constructive feedback to the practitioner/user regarding MRI imaging skills and proficiency. Starting at step 410, a user 310, preferably after a registration process, logs into the web application server 320 (e.g., screenshot 510, FIG. 5A) to commence the below discussed MRI simulation/test process. Preferably, a first decision is made as to whether the user 310 is a student or manager (e.g., mentor, instructor, evaluator, etc.) of a student (step 420). If determined to be a manager, then the process 400 for evaluating the student's MRI simulation, as discussed further below, is performed (step 430).

Figure 5B:
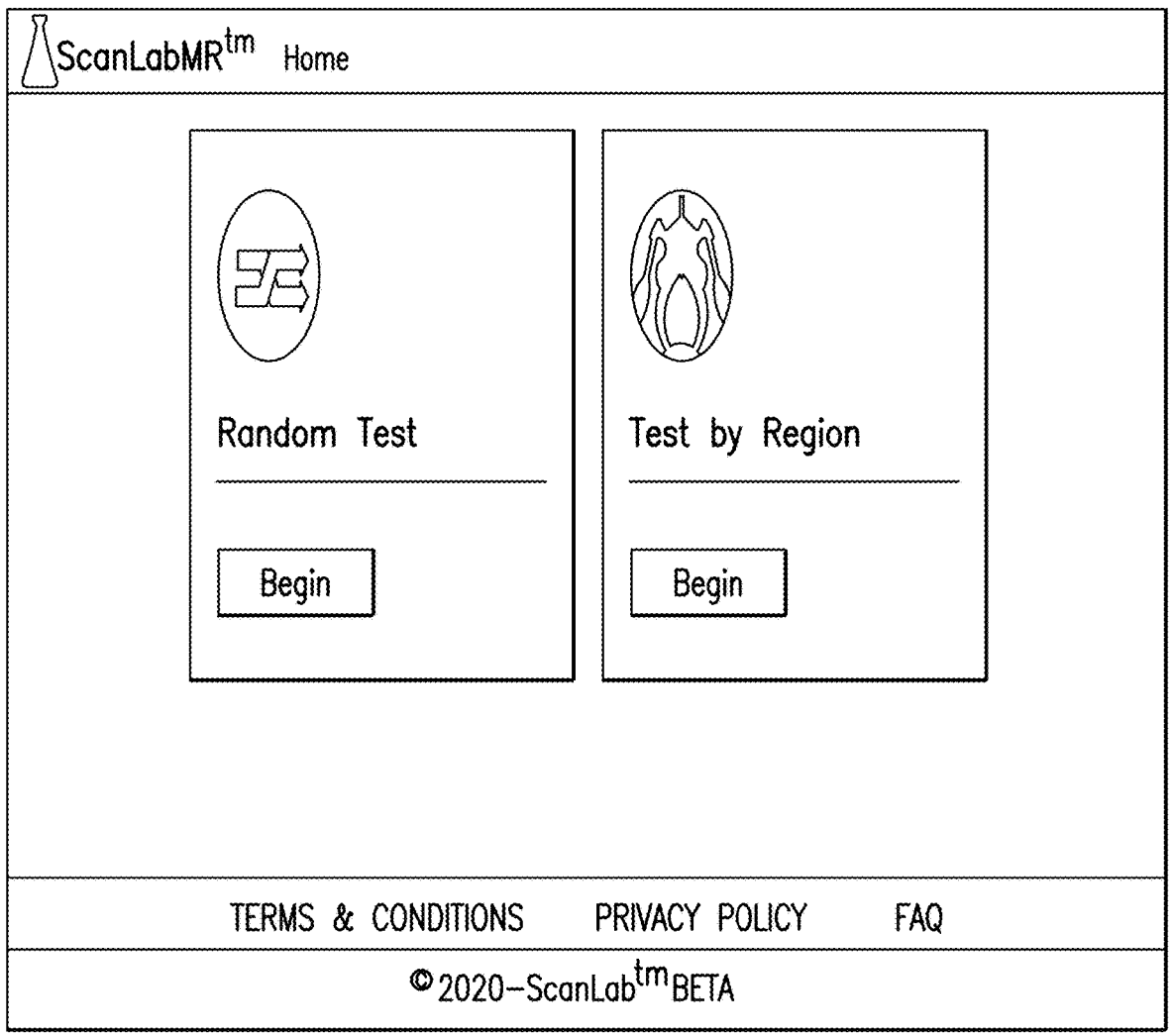
Figure 5C:
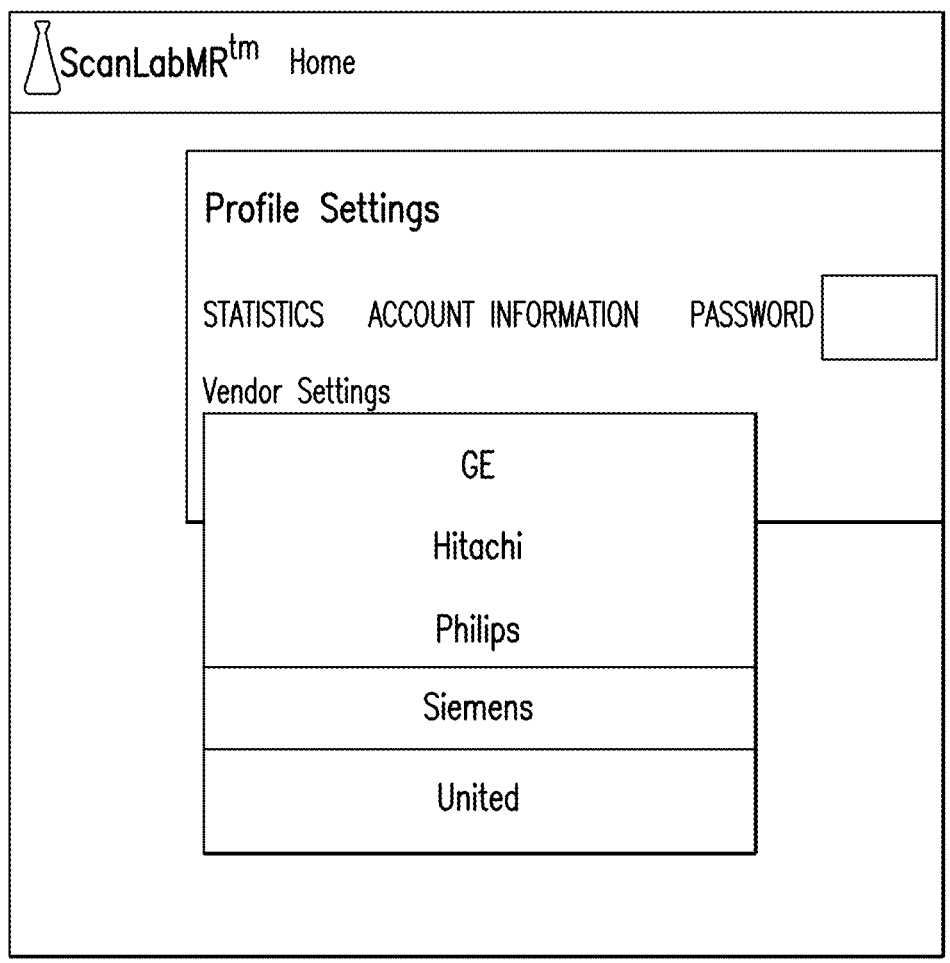
Figure 5D:
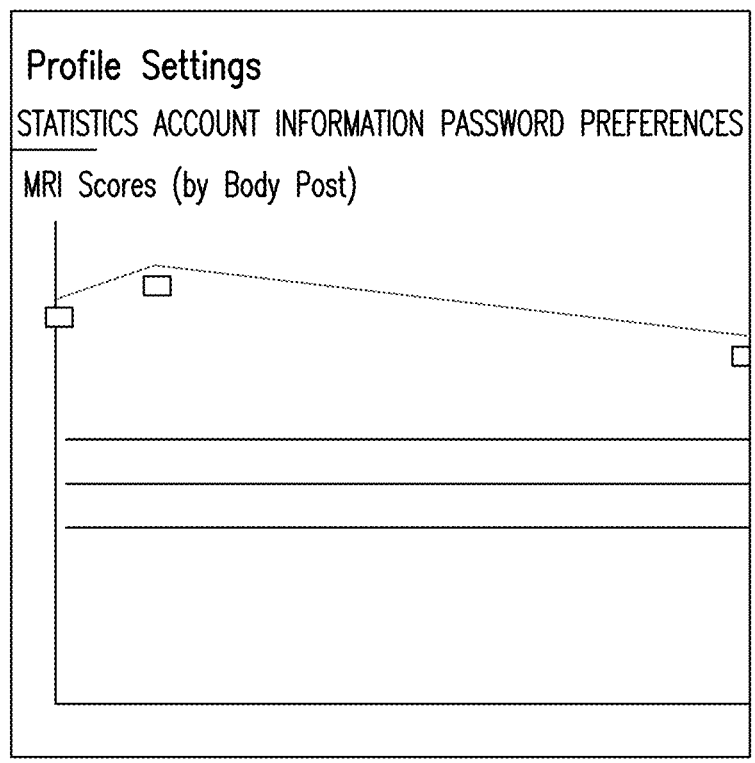

In the event the user 310 is determined to be a student (step 420), the user may first be directed to a web page in which they can edit their user profile and/or select whether to take a randomized MRI simulation test or choose a specific body region they desire to conduct an MRI simulation (e.g., screen shot 520, FIG. 5B). It is also noted that the application of the web application server 320 may be configured to enable a user 310 to select system preference settings for a certain type/configuration for an MRI simulation to be conducted (e.g., screenshot 530, FIG. 5C) and/or select the metrics/profile settings in which a user 310 can preferably visualize their examination and critical thinking scores across numerous time points within their user profile (e.g., screenshot 540, FIG. 5D).

Figure 5E:
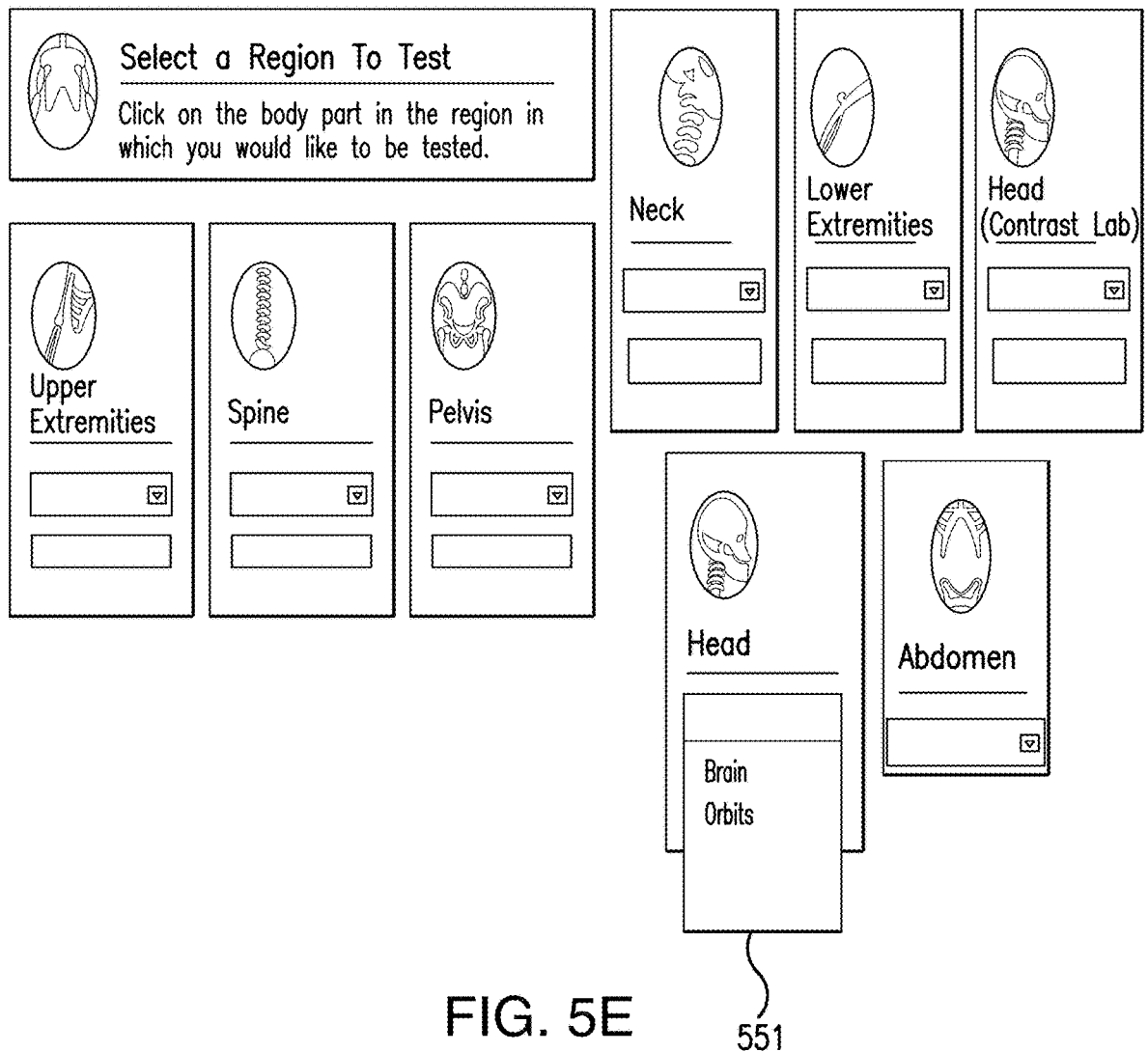
Figure 5F:
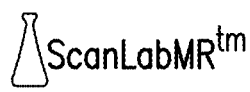

Progressing to step 440, a user 310 may preferably select a body region for which to conduct the MRI simulation upon (e.g., screenshot 550, FIG. 5E). For instance, and as depicted, in accordance with an illustrated embodiment, the user 310 may choose between differing body regions (e.g., Neck, Lower Extremities, Head, Abdomen, Upper Extremities, Spine, Pelvis) for conducting the MRI simulation upon. Additionally, each selected body region (e.g., Head) may have an associated drop-down menu (e.g., 551) for selecting a separate simulation/exam (e.g., Brain, Orbits, IACs and Pituitary). Once a body region has been selected for conducting the MRI simulation (step 440), the user then selects a specific MRI simulation/exam to perform, step 450, whereupon safety questions may then be presented to the user 310, step 460 (e.g., screen shot 552, FIG. 5F). Preferably, prior to the MRI simulation/exam, the user 310 is requested to review an MRI screening form, which enables the user to not only be evaluated on competency in MRI safety concepts, but also provides proficiency in MRI safety concerns prior to engaging in an clinical MRI scan.

Figure 5G:
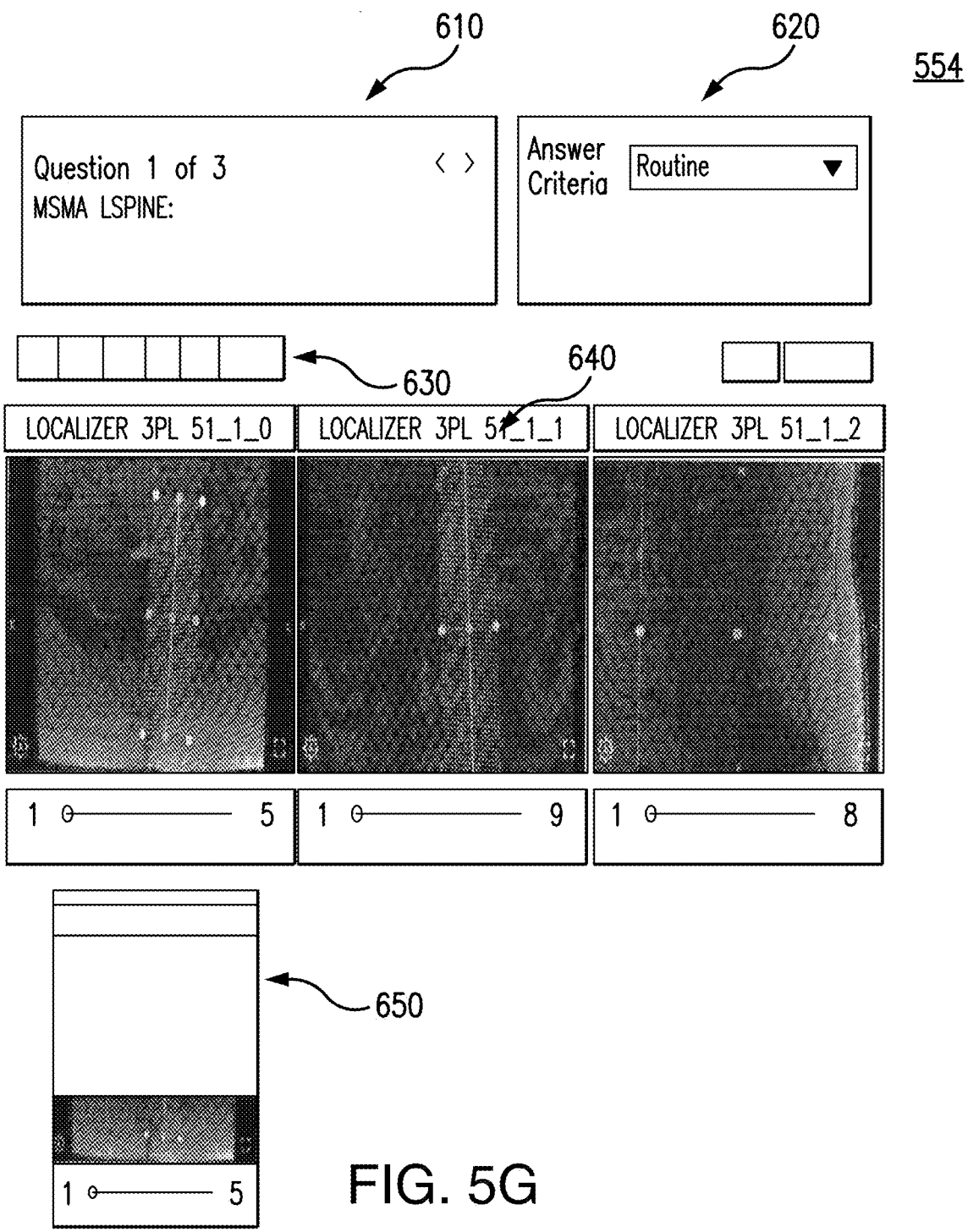
Figure 5H:
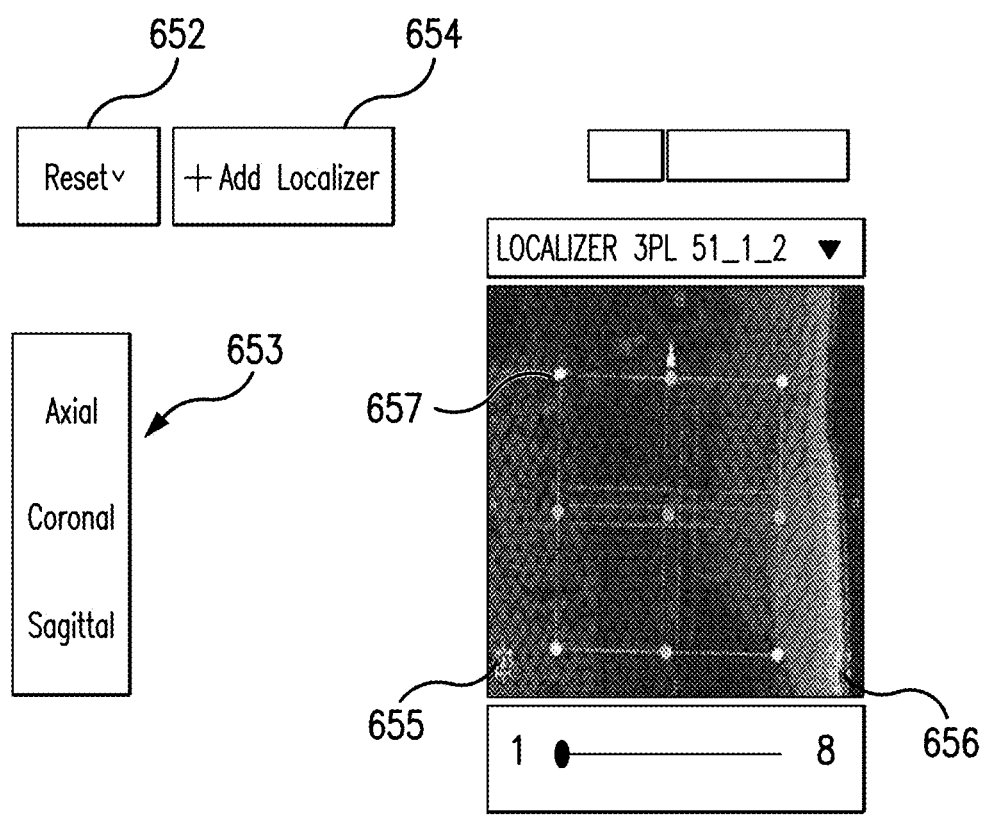

Next, the application commences the user selected MRI simulation/exam, such as by creating MRI slice prescriptions, step 470. In this regard, and starting at screen shot 554 (FIG. 5G), within the selected MRI simulation, a user 310 is preferably presented with a set of questions/directions 610 on which scan to perform, which answer criteria 620 aids the user in understanding certain anatomy during an MRI scan. Additionally, the MRI simulation may preferably provide the following user Interface (UI) scanner tools: 1) the ability to be able to move, resize, rotate, pan, zoom an MRI scan 630; 2) the ability to change the windowing/lighting of the MRI image 640; and 3) provide the user with the ability to review previous MRI images preferably taken in the drop down above each MRI image 650. With reference now to screen shot 556 (FIG. 5H), the application UI is also preferably configured to provide a Reset Button 652 which allows the user 310 to return back to an axial, coronal, or sagittal setting 653, and +Add Localizer 654 whereby the user can add their own localizer if they don't prefer the one presented by the application to the user. With continuing reference to screen shot 556, it is noted that the "A" 655 at the bottom left corner is functional to reset the image to its starting point and the box 650 in the lower right corner enables the user 310 to bring the image into full screen whereby the arrow 657 on the localizer preferably indicates phase encoding direction.

Figure 5I:
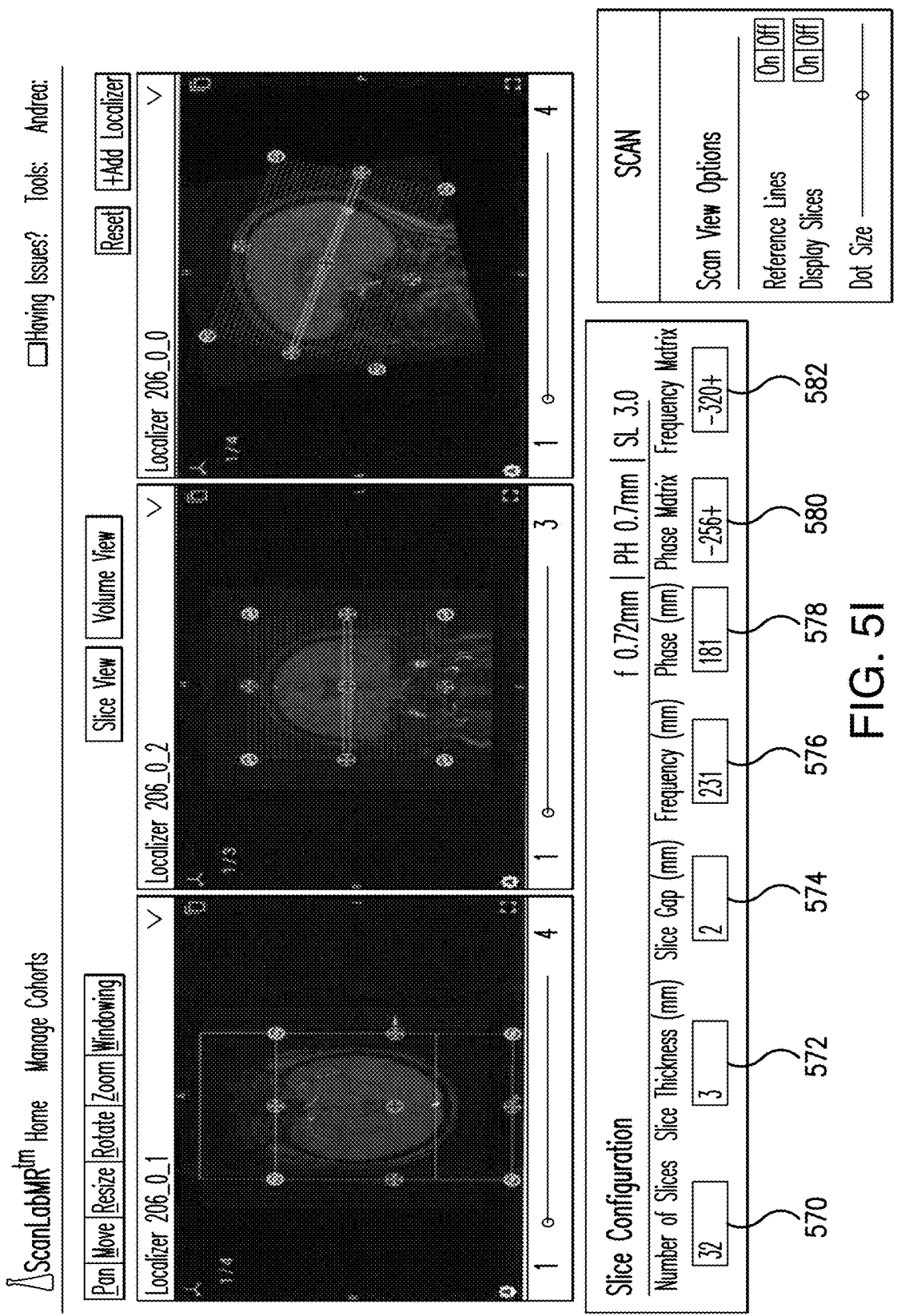

In accordance with certain embodiments, shown in FIG. 5I is screen shot 559 depicting a user interface, preferably provided via the Resolution Lab API 332 (FIG. 3) depicting the various configuration settings presented to a user 310 for prescribing a the user selected MRI simulation/exam, including (but limited to): number of slices 570; slice thickness 572; slice gap 574; frequency 576; phase 578; phase matrix 580 and frequency matrix 582.

Figure 5J:
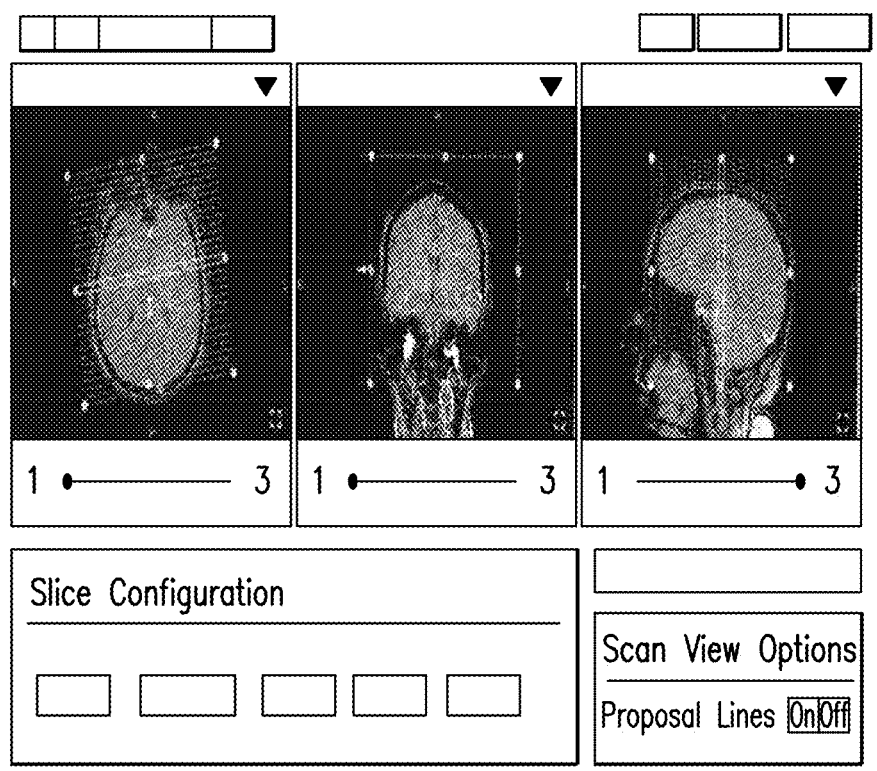
Figure 5K:
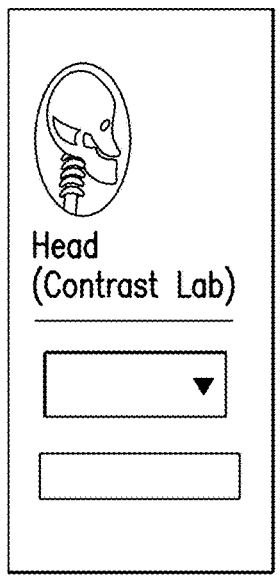
Figure 5L:
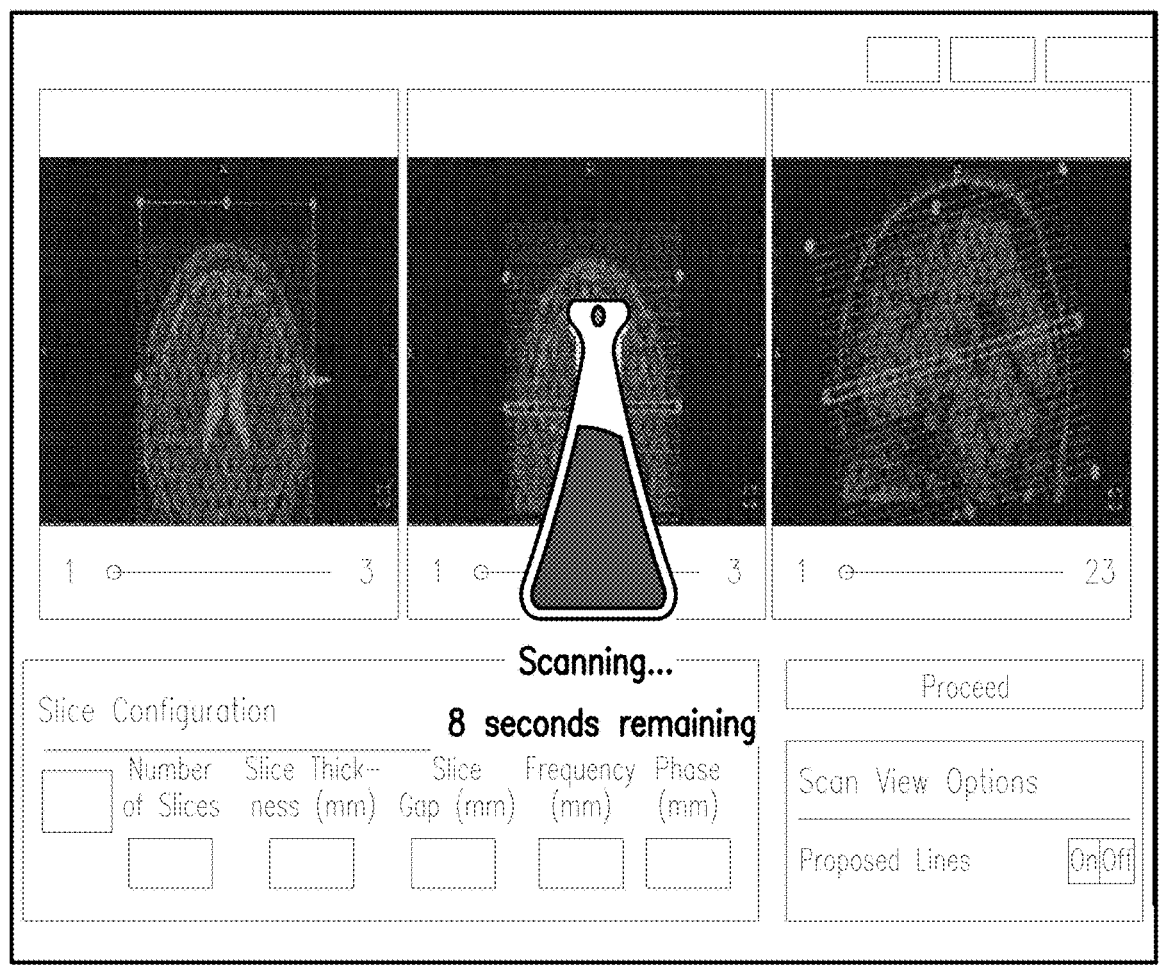
Figure 5M:
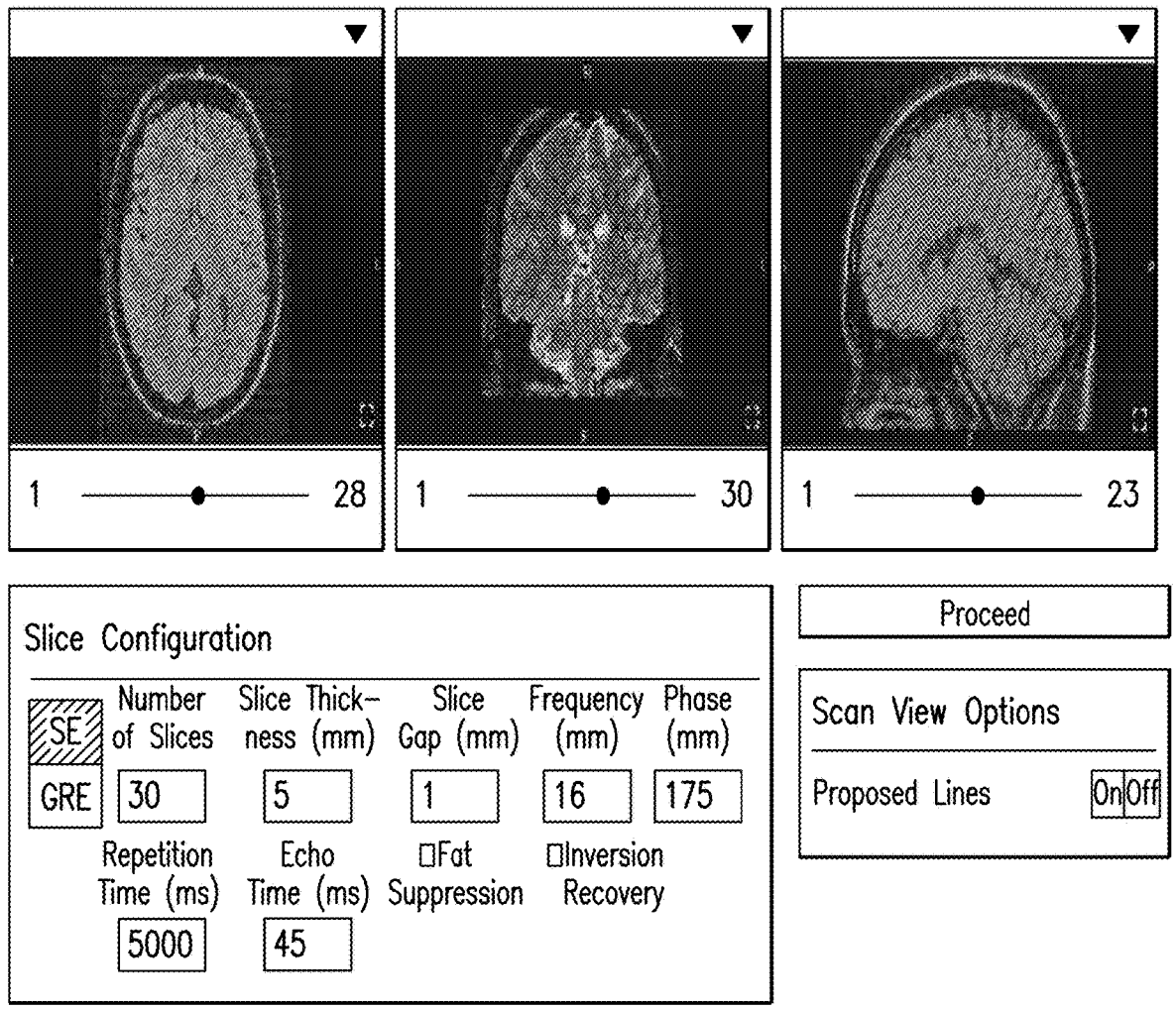

Referring now to screen shot 558 (FIG. 5J), and with regard to evaluating the User 310, the user may evaluated/graded on MRI slice prescription based on the following criteria: Field Of View; Slice Thickness; Slice Coverage Slice Gap; and In-Plane Rotation. Preferably, and in accordance with the illustrated embodiments, a quantitative score is provided for the user's performance regarding the conducted MRI simulation/test based on a deviation algorithm from acceptable MRI ranges and angles. With reference to screen shot 560 (FIG. 5K), it is to be appreciated that the Application provides Contrast Lab Examinations whereby the contrast lab interface preferably supports spin echo and gradient echo sequences with the option to adjust: TR; TE; Fat Suppression; Inversion/TI and Flip Angle. With reference to screen shots 562 and 564 (FIGS. 5L and 5M), it is to be further appreciated that preferably after the user selects the "scan" button for performing the MRI simulation/evaluation, generated on a display are images with the exact slice geometry and applied contrast parameters for the user to view their results.

With return reference to process 400 (FIG. 4) and with reference to screen shot 566 (FIG. 5N), the user 310 is then preferably required to answer critical questions, step 480, such that after completing the slice/contrast prescription portion of the aforesaid MRI simulation/examination, the user 310 is then evaluated on various aspects of MRI to determine competency and categorical knowledge. For instance, included categories include (but are not to be understood to be limited to): Safety; Pathology Recognition; Anatomy; Clinical Procedures; Parameters and Trade-Offs; and Artifacts. With reference to screen shot 568 (FIG. 5O), it is to be further appreciated that the User 310 may also preferably be tested on their understanding of angiography contrast exam timing. For instance, when the user selects "Start Contrast Fluoro", an animation may begin showing the exact flow of contrast, afterwards the user selects the "Stop Fluoro/Start Scan", preferably when they believe the Fluoro should be stopped.

Figure 5P:
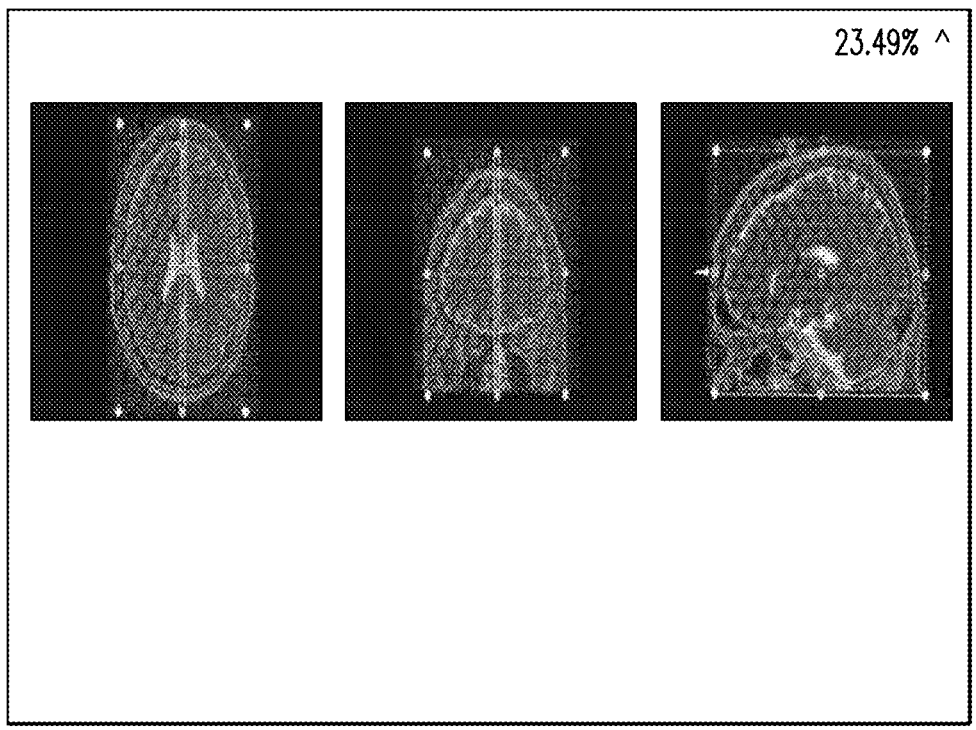

At step 490 of process 400 (FIG. 4), and with reference to screen shot 570 (FIG. 5P), the User 310 is then preferably provided with feedback regarding their performed MRI simulation/exam such that after the completion of a given examination, the user is preferably provided with a comprehensive report as to the reason(s) that they were awarded a certain score on the slice prescription portion of the aforesaid conducted MRI simulation/exam. It is to be appreciated that feedback may be provided with color, or other indication schema, whereby displayed is Green, Yellow, or Red varying on the amount in which that action effected the users score, such that the user is also able to view their scans for review with written feedback from a manager/instructor. And as show in screen shot 572 (FIG. 5Q), preferably after the completion of a given MRI simulation/examination, the user is presented with a comprehensive report on questions that they answered during the critical thinking questions within the MRI simulation/examination, whereby an explanation of why they got the answer correct or not is preferably provided.

Figure 5S:
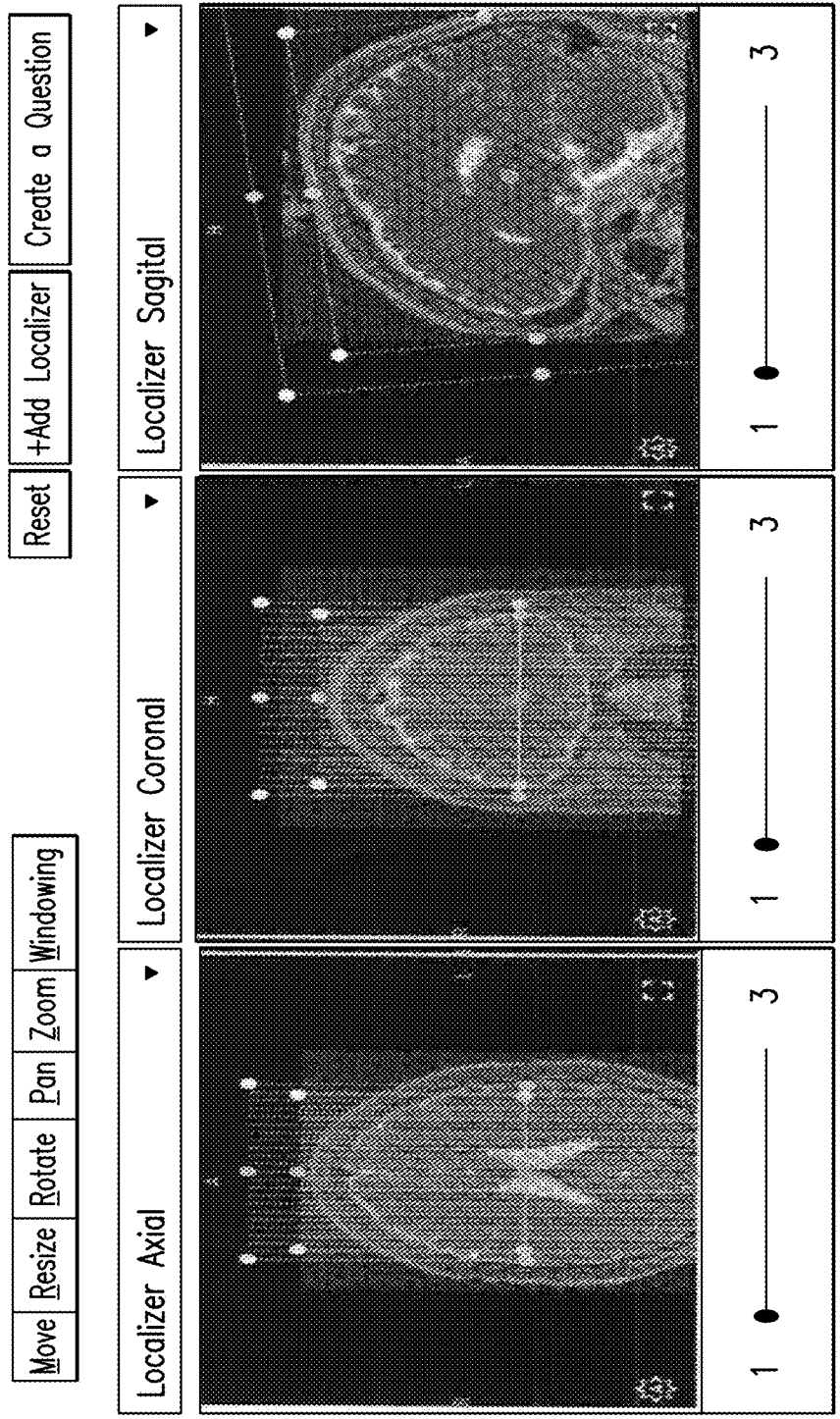

Returning to step 430 of process 400 (FIG. 4), and upon a manager/instructor logging in (step 420), and with reference to screen shot 574 (FIG. 5R), in accordance with the illustrated embodiments, the application is configured to assign mangers to cohorts such that managers are able to search for certain user's (students) and access each selected user's scores to view associated scans and critical thinking questions, such that the application provides the ability to build cohorts of managers/users (students). And with reference to screen shot 576 (FIG. 5S), with regards to scoring, it is to be appreciated that for each exam provided, there is preferably a minimum and maximum range that is accepted, and grades are preferably scaled outside of these parameters based on how the user deviates from the ranges defined.

Accordingly, what has been described in accordance with the certain illustrated embodiments is web based simulator application configured to provide student MRI user's to be graded based on expertise and vocation mastery. For instance, grading may be provided on the following exemplary acceptable MRI ranges: correct slice angles; how large or small the field of imaging is; how thick a slice can be; how many slices are needed to cover a certain body part (e.g. a brain, wrist, knee); how much space is between slices; image parameters that make an image look a certain way (fluid dark, fat bright, etc). And based on the user's deviation from the correct ranges, a score is generated whereby points may be deducted for improper deviation while providing internal gradient rubric and algorithm. For instance, a simulated MRI exam may consist of numerous multiple choice questions, and numerous slice positioning questions (as described above). The multiple choice questions may be sorted into various categories and presented so as to reproduce the skill/thought processes required for performing an MRI examination on an actual patient. As a result, application uses may include a hiring tool, an internal quality tool, or an educational tool.

With certain illustrated embodiments described above, it is to be appreciated that various non-limiting embodiments described herein may be used separately, combined or selectively combined for specific applications. Further, some of the various features of the above non-limiting embodiments may be used without the corresponding use of other described features. The foregoing description should therefore be considered as merely illustrative of the principles, teachings and exemplary embodiments of this invention, and not in limitation thereof.

It is to be understood that the above-described arrangements are only illustrative of the application of the principles of the illustrated embodiments. Numerous modifications and alternative arrangements may be devised by those skilled in the art without departing from the scope of the illustrated embodiments, and the appended claims are intended to cover such modifications and arrangements.

What is claimed is:

1. A computer implemented method for simulation of a Magnetic Resonance Imaging (MRI) medical procedure, the computer implemented method executed within a computer system comprising a computer processor connected to a storage medium, and a user interface having a user terminal, the method comprising the steps of:

selecting, for user interaction on a computer display, MRI settings associated with a third party MRI vendor selected from a listing of certain third party vendors;

visually displaying, at the user terminal for user selection, one or more criteria for initiating simulation of the MRI procedure in accordance with the settings of the selected third party vendor;

visually displaying, at the user terminal for user selection, one or more MRI examination procedures to be simulated based upon the user selected criteria for simulation of the MRI procedure;

visually displaying, at the user terminal, a virtual MRI interface for accepting user input for configuring imaging to be initiated for a user selected MRI examination procedure to be simulated based upon the user selected criteria for simulation of the MRI procedure;

visually displaying, at the user terminal, one or more critical questions relating to the user selected MRI examination procedure to be simulated based upon the user selected criteria for simulation of the MRI procedure, wherein a user provides one or more responses to the one or more critical questions;

simulating, by the processor, the user selected MRI examination procedure based upon the user selected criteria for simulation of the MRI procedure to generate resulting MRI images;

visually displaying, at the user terminal, the generated resulting MRI images;

determining, by the processor, based upon prescribed criteria, a deviation value from which the generated resulting MRI images deviate from acceptable MRI images relating to the user selected MRI examination procedure; and determining, by the processor, a score value for the user's simulated MRI examination procedure based upon the determined deviation value and the user's response to the one or more critical questions.

2. The computer implemented method as recited in claim 1, wherein the one or more criteria includes selecting a type of virtual MRI scanner from a plurality of virtual MRI scanner types stored in the storage medium.

3. The computer implemented method as recited in claim 1, wherein the one or more criteria includes selecting a virtual anatomic model of a patient body component from a plurality of anatomic models stored in the storage medium.

4. The computer implemented method as recited in claim 1, wherein a plurality of MRI examination procedures are stored in the storage medium for user selection.

5. The computer implemented method as recited in claim 1, further including, visually displaying, at the user terminal, one or more safety questions relating to the user selected MRI examination procedure to be simulated based upon the user selected criteria for simulation of the MRI procedure, wherein the user provides one or more responses to the one or more safety questions.

6. The computer implemented method as recited in claim 1, wherein the step of visually displaying, at the user terminal, the virtual MRI interface includes accepting user input for configuring one or more of: MRI slice positions; MRI pulse sequences, one or more entry points into patient tissue, one or more target locations to be treated, and a first target location to be approached first.

7. The computer implemented method as recited in claim 6, wherein the virtual MRI interface provides a same interface as associated with actual MRI scanner of the selected third party vendor.

8. The computer implemented method as recited in claim 1, wherein the one or more critical questions includes at least one question selected from one or more of the categories relating to: Safety; Pathology Recognition; Anatomy; Clinical Procedures; Parameters and Trade-Offs; and Artifacts.

9. The computer implemented method as recited in claim 1, wherein the one or more critical questions includes at least one question relating to angiography contrast exam timing.

10. The computer implemented method as recited in claim 1, wherein the prescribed criteria for determining the deviation value is dependent upon one or more of: image slice angles; a size of a field of imaging; image slice thickness; proper number of slices required to cover a certain body portion; and spacing between image slices.

11. The computer implemented method as recited in claim 1, further including, storing, by the processor, the user's determined score value in the storage medium.

12. The computer implemented method as recited in claim 11, further including visually displaying, at an instructor terminal, an instructor interface providing selective instructor access to visually display one or more generated resulting MRI images in association with the determined user score value retrieved from the storage medium associated with one or more users.

13. A computer system for simulation of a Magnetic Resonance Imaging (MRI) medical procedure, the computer implemented method executed within a computer system comprising a computer processor connected to a storage medium, and a user interface having a user terminal, comprising:
  a memory configured to store instructions;
  a processor disposed in communication with said memory, wherein said processor upon execution of the instructions is configured to:
  visually display, at the user terminal for user selection, MRI settings associated with a third party MRI vendor selected from a listing of certain third party vendors for initiating simulation of the MRI procedure;
  visually display, at the user terminal for user selection, one or more MRI examination procedures to be simulated based upon the user selected criteria for simulation of the MRI procedure in accordance with the settings of the selected third party vendor;
  visually display, at the user terminal, a virtual MRI interface, contingent upon the selected third party MRI vendor, for accepting user input for configuring imaging to be initiated for a user selected MRI examination procedure to be simulated based upon the user selected criteria for simulation of the MRI procedure;
  visually display, at the user terminal, one or more critical questions relating to the user selected MRI examination procedure to be simulated based upon the user selected criteria for simulation of the MRI procedure, wherein a user provides one or more responses to the one or more critical questions;
  simulate, by the processor, the user selected MRI examination procedure based upon the user selected criteria for simulation of the MRI procedure to generate resulting MRI images;
  visually display, at the user terminal, the generated resulting MRI images;
  determine, by the processor, based upon prescribed criteria, a deviation value from which the generated resulting MRI images deviate from acceptable MRI images relating to the user selected MRI examination procedure; and
  determine, by the processor, a score value for the user's simulated MRI examination procedure based upon the determined deviation value and the user's response to the one or more critical questions.

14. The computer system as recited in claim 13, wherein the one or more criteria includes selecting a type of virtual MRI scanner from a plurality of virtual MRI scanner types stored in the storage medium.

15. The computer system as recited in claim 13, wherein the one or more criteria includes selecting a virtual anatomic model of a patient body component from a plurality of anatomic models stored in the storage medium.

16. The computer system as recited in claim 13, wherein a plurality of MRI examination procedures are stored in the storage medium for user selection.

17. The computer system as recited in claim 13, further including, visually displaying, at the user terminal, one or more safety questions relating to the user selected MRI examination procedure to be simulated based upon the user selected criteria for simulation of the MRI procedure, wherein the user provides one or more responses to the one or more safety questions.

18. The computer system as recited in claim 13, wherein the step of visually displaying, at the user terminal, the virtual MRI interface includes accepting user input for configuring one or more of: MRI slice positions; MRI pulse sequences, one or more entry points into patient tissue, one or more target locations to be treated, and a first target location to be approached first.

19. The computer system as recited in claim 18, wherein the virtual MRI interface provides a same interface as associated with actual MRI scanner of the selected third party MRI vendor.

20. The computer system as recited in claim 13, wherein the one or more critical questions includes at least one question relating to angiography contrast exam timing.

* * * * *